United States Patent [19]
Liu et al.

[11] Patent Number: 4,582,853

[45] Date of Patent: Apr. 15, 1986

[54] TREATMENT OF COCCIDIOSIS WITH ANTIBIOTIC X-14934A

[75] Inventors: Chao-Min Liu; John Westley, both of Cedar Grove, N.J.

[73] Assignee: Hoffmann-La Roche Inc., Nutley, N.J.

[21] Appl. No.: 693,448

[22] Filed: Jan. 22, 1985

Related U.S. Application Data

[62] Division of Ser. No. 518,233, Jul. 28, 1983, Pat. No. 4,510,317.

[51] Int. Cl.[4] .............................................. A61K 31/35
[52] U.S. Cl. .................................................... 514/460
[58] Field of Search ........................ 549/343; 514/460

[56] References Cited

U.S. PATENT DOCUMENTS

| | | | |
|---|---|---|---|
| 3,953,474 | 4/1976 | Hamill | 549/343 |
| 4,359,583 | 11/1982 | Mizutani et al. | 549/343 |
| 4,431,665 | 2/1984 | Kluge et al. | 549/343 |

Primary Examiner—Nicky Chan
Attorney, Agent, or Firm—Jon S. Saxe; Bernard S. Leon; Richard J. Mazza

[57] ABSTRACT

The present invention relates to a novel polyether ionophore antibiotic of the formula

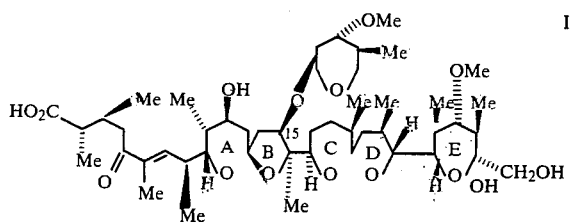

and its pharmaceutically acceptable salts.

The compound of formula I and its salts exhibit activity as an antibacterial agent and as an anticoccidial agent.

1 Claim, No Drawings

TREATMENT OF COCCIDIOSIS WITH ANTIBIOTIC X-14934A

DESCRIPTION OF THE INVENTION

This is a division of application Ser. No. 518,233 filed July 28, 1983, now U.S. Pat. No. 4,510,317.

The present invention relates to a novel polyether ionophore antibiotic of the formula

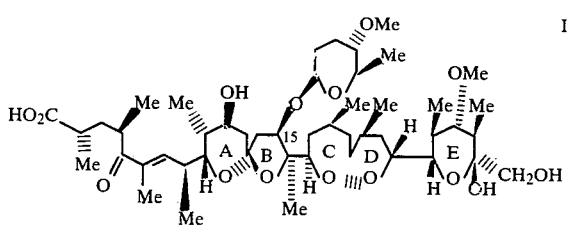

and its pharmaceutically acceptable salts.

The shorthand expression Me is utilized above to represent methyl.

The compound of formula I and its salts exhibit activity as an antibacterial agent and as an anticoccidial agent.

Antibiotic X-14934A is the designation given to a crystalline antibiotic produced by a Streptomyces organism, lyophilized tubes of which were deposited with the U.S. Department of Agriculture, Agricultural Research Service, Northern Regional Research Laboratories (NRRL), Peoria, Ill. The culture, given the identification number NRRL 15518 by NRRL has been made available to the public through NRRL.

Antibiotic X-14934A is a polyether antibiotic and forms a variety of pharmaceutically acceptable salts. These salts are prepared from the free acid form of the antibiotic by methods well-known for compounds of the polyether type in the art; for example, by washing the free acid in solution with a suitable base or salt. Examples of such pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

Examples of organic bases forming pharmaceutically acceptable salts with the polyether compounds are lower primary, secondary and tertiary alkyl amines, and hydroxy alkylamines such as ethylamine, isopropylamine, diethylamine, methyl-n-butylamine, ethanolamine and diethanolamine.

MORPHOLOGICAL CHARACTERISTICS

A representative strain of Streptomyces X-14934 has the following characteristics:

1. Microscopic characteristics. Culture X-14934 grows in agar media of various compositions giving a submerged mycelium which penetrates into the agar and does not fragment with age, and an aerial mycelium that partially differentiates into spore chains. These chains are spiral in form, and have more than 10 spores each. The spores cannot be seen individually due to a sheath covering the whole chain and becoming wrinkled upon dehydration. The spores are smooth, and they measure, in average, 0.6 $\mu$m by 1.1 $\mu$m.

Paper chromatographic analysis of whole cell hydrolyzates revealed the presence of LL-diaminopimelic acid, which confirms the identification of this organism as a strain of the genus Streptomyces.

2. Macroscopic characteristics. In the Table below the characteristics of the growth, degree of sporulation, and color of the aerial mass and of the reverse mycelium in several media, are presented. The data have been recorded after 14 days of incubation at 28° C.

| Medium | Amount of growth and degree of sporulation | Color of the aerial mass (1) | Color of the reverse mycelium (1) |
| --- | --- | --- | --- |
| Yeast-malt extract (ISP-2) | abundant growth; no sporulation | oyster white (b) | straw (2 fb) |
| Oatmeal agar (ISP-3) | abundant growth; hygroscopic; well sporulated | beige brown (3 ig) with white specks | silver gray (3 fe) with white specks |
| Inorganic salts-starch agar (ISP-4) | abundant growth and good sporulation | silver gray pastel yellow (3 fe) | (1½ fb) |
| Glycerol-asparagine agar (ISP-5) | poor growth; scanty sporulation | white (a) | white (a) |

(1) The color code is that of the Color Harmony Manual 4th edition, Container Corporation of America, 1958.

3. Physiological characteristics. Strain X-14934 utilizes glucose, L-arabinose, sucrose, i-inositol, mannitol, fructose, rhamnose and raffinose, and less effectively, xylose as sole carbon sources for growth. The utilization of cellulose is negative.

Production of H$_2$S, as indicated by darkening in peptone-yeast extract-iron agar (ISP 6) is positive, and a dark color (melanin) develops in tyrosine-containing medium (ISP 7). Nitrate reduction is negative. Gelatin, starch and casein hydrolysis are positive. There is no growth at NaCl concentration of 3.5% or higher.

4. Comparison with known Streptomyces species. On the basis of color of the spore mass, shape of the spore chains, spore surface and production of melanoid pigments, as well as the hygroscopic character of the colonies on some media and the carbon utilization tests, strain X-14934 can be assigned to the species *Streptomyces hygroscopicus*.

The Streptomyces X-14934 described herein includes all strains of Streptomyces which form a compound as claimed in the present application and which cannot be definitely differentiated from the strain NRRL and its subcultures including mutants and variants. The claimed compound is described herein and after this identification is known, it is easy to differentiate the strains producing this compound from others.

Streptomyces X-14934 when grown under suitable conditions, produces an antibiotic X-14934A. A fermentation broth containing Streptomyces X-14934 is prepared by inoculating spores or mycelia of the organism producing the antibiotic into a suitable medium and then cultivating under aerobic conditions. For the production of the antibiotic, cultivation on a solid medium is possible but for production in large quantities, cultivation in a liquid medium is preferable. The temperature of cultivation may be varied over a wide range, 20°–35° C., within which the organism may grow but a temperature of 26°–30° C. and a substantially neutral pH are preferred. In the submerged aerobic fermentation of the organism for the production of antibiotic X-14934A, the medium may contain as the source for carbon, a commercially available glyceride oil or a carbohydrate such as glycerol, glucose, maltose, lactose, dextrin, starch, etc. in pure or crude states and as the source of nitrogen, an organic material such as soybean meal, distillers' solubles, peanut meal, cotton seed meal, meat extract, peptone, fish meal, yeast extract, corn steep liquor, etc. and when desired inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of antibiotic X-14934A.

Antibiotic X-14934A has a toxicity ($LD_{50}$) in mice of 25 mg/kg (PO) and 7.75 mg/kg (IP) as the monohydrate sodium salt.

The following examples set forth a method by way of example to produce X-14934A:

EXAMPLE 1

Streptomyces sp. X-14934 is grown and maintained on a starch casein agar slant having the following composition (grams/liter distilled water):

| Soluble starch | 10.0 |
|---|---|
| Casein | 1.0 |
| $K_2HPO_4$ | 0.5 |
| $MgSO_4$ | 0.5 |
| Agar | 20.0 | pH is adjusted to 7.4 with NaOH before autoclaving.

A slant inoculated with culture X-14934 is incubated at 28° C. for 7–14 days. A chunk of agar containing spores and mycelia from the incubated culture slant is used to prepare vegetative inoculum by inculating it into a 500-ml Erlenmeyer flask containing 100 ml of medium having the following composition (grams/liter tap water):

| Soyalose | 10.0 |
|---|---|
| Cerelose | 20.0 |
| $Na_2SO_4$ | 1.0 |
| $CaCO_3$ | 0.2 |
| $CoCl_2.6H_2O$ | 0.001 | pH is adjusted to 6.0 before sterilization.

The inoculated medium is incubated at 28° C. for 4 days on a rotary shaker operating at 250 rpm. Two 30-ml portions of the resulting culture are used to inoculate two 6-liter Erlenmeyer flasks each containing 2 liters of medium having the composition described above. These inoculated 6-liter Erlenmeyer flasks are incubated for 4 days at 28° C. on a rotary shaker running at 250 rpm. The four liters of resulting vegetative growth are used to inoculate a 100-gallon fermentor containing 60 gallon of production medium having the following composition (grams/liter tap water):

| Cerelose | 20.0 | |
|---|---|---|
| Soyalose | 10.0 | pH is adjusted to 6.0 |
| $Na_2SO_4$ | 1.0 | before sterilization |
| $CaCO_3$ | 0.2 | |
| $CoCl_2.6H_2O$ | 0.001 | |

SAG 4130 Antifoam (added as required during fermentation)

The inoculated tank is aerated with compressed air at 3 cubic feet per minute, and is stirred with agitators at 280 rpm. The fermentation is carried out at 28° C. for 97 hours.

EXAMPLE 2

Isolation of X-14934A, sodium salt

Step A: To the whole broth from a sixty-gallon (227.1 liters) fermentation as set forth in Example 1 was added, after 139 hrs growth, an equal volume of ethyl acetate. After stirring for one hour the solvent layer was separated and the aqueous phase was extracted again with an equal volume of ethyl acetate as before. The two solvent phases were pooled and were concentrated to 2.6 liters under reduced pressure.

Step B: The ethyl extract was further concentrated to an oil. The oil was dissolved in n-hexane and was extracted five times with an equal volume of acetonitrile followed by one extraction with acetonitrile/methanol (9:1). The acetonitrile and acetonitrile/methanol (9:1) extracts were pooled and the solvent was removed under reduced pressure. The residue thus obtained was dissolved in ethyl acetate and was washed in turn with 1N HCl, $Na_2CO_3$ (saturated at room temperature) and $H_2O$. The solvent phase was dried over $Na_2SO_4$ and was concentrated to an oil (38 g) under reduced pressure.

Step C: The resulting oil of Step B was dissolved in methylene chloride and was chromatographed on a methylene chloride slurry packed 500 g silica gel (Davison grade 62) column. The column was eluted with 2 liters methylene chloride, 4 liters ethyl acetate/hexane (7:3), 2 liters ethyl acetate/methanol (95:5) and 2 liters ethyl acetate/methanol (9:1).

Fractions 20 ml each were collected and fraction numbers 490–512 were pooled. The solvent was removed in reduced pressure and the residue (8 g) was rechromatographed on a methylene chloride slurry packed 250 g silica gel column. This column was eluted with 2 liters diethyl ether, 2 liters diethyl ether/ethanol (20:0.5). Fractions of 20 ml each were collected.

Step D: Fraction numbers 60–100 from the 250 g silica gel column described above in Step C were pooled and solvent was removed under reduced pressure. Crystallization from acetonitrile/water yielded crystalline antibiotic X-14934A-Na salt dihydrate. Mp. 156°–158° C. Microanalysis calculated for $C_{48}H_{79}O_{15}$·$Na.2H_2O$ (955.18): Calculated: C 60.36, H 8.76, Na 2.41, $H_2O$ 3.77. Found: C 60.62, 60.90; H 8.96, 9.11; Na 2.34, $H_2O$ 4.52.

EXAMPLE 3

Preparation of X-14934A, rubidium salt

A solution of 100 mg antibiotic X-14934A-Na salt in methylene chloride was first washed with 1N HCl, followed by water wash and then four times with an aqueous solution RbOH. The solvent phase was dried by filtering through celite and was concentrated in reduced pressure and was crystallized from acetonitrile by the addition of water. Recrystallization yielded crystals suitable for X-ray analysis. Calculated for $(C_{48}H_{79}O_{15})_2Rb(H_2O)_2$: C 60.25, H 8.53, Rb 4.47, $H_2O$ 1.88. Found: C 59.73, H 8.41, Rb 4.63, $H_2O$ 1.74.

The antimicrobial activity of the antibiotic X-14934A is shown by the the following table:

|  | Organism | ATCC NO. | Minimum Inhibitory Concentration (MIC)* (MCG/ML) |
|---|---|---|---|
| G−rods | Pseudomonas aeruginosa | 8705 | >1000 |
|  | Proteus vulgaris | 6380 | >1000 |
|  | Escherichia coli | 27856 | >1000 |
|  | Klebsiella pneumoniae | 27858 | >1000 |
|  | Serratia marcescens | 27857 | >1000 |
|  | Serratia sp. | 93 | >1000 |
|  | Acinetobacter calcoaceticus | 10153 | >1000 |
| G+ cocci | Streptococcus faecium ATCC | 8043 | 0.9 |
|  | Staphylococcus aureus | 6538P | 1.9 |
|  | Micrococcus luteus | 9341 | 7.9 |
| G+ rods | Bacillus megaterium | 8011 | 3.9 |
|  | Bacillus sp. E | 27359 | 0.45 |
|  | Bacillus subtilis | 558* | 3.9 |
|  | Bacillus sp. TA | 27860 | 3.9 |
| G+ filaments | Mycobacterium phlei | 355 | 7.9 |
|  | Streptomyces cellulosae | 3313 | 15.7 |
| Molds | Paecilomyces varioti | 25820 | 62.5 |
|  | Penicillium digitatum | 26821 | 125 |
| Yeasts | Candida albicans | 477* | 7.9 |
|  | Saccharomyces cerevisiae | 4226 | 125 |

*NRRL Number
*LOWEST CONCENTRATION STILL SHOWING ZONE OF INHIBITION BY THE AGAR-DIFFUSION WELL METHOD.

As is indicated above, antibiotic X-14934A and its salts possess the property of adversely affecting the growth of certain Gram-positive bacteria. It is useful in wash solutions for sanitary purposes as in the washing of hands and the cleaning of equipment, floors or furnishings of contaminated rooms or laboratories. It is useful also for suppressing the growth of sensitive organisms in plate assays and other microbiological media.

Antibiotic X-14934A exhibits activity against *Treponema hyodysenteriae,* a causative agent of swine dysentery. Marked activity was shown for the antibiotic at concentrations as low as 1 mcg/ml.

Antibiotic X-14934A exhibits activity as coccidiostat agent

This anti-coccidial activity is demonstrated on laboratory chickens as follows:

TEST METHOD

This test utilizes ten chickens per drug group. Ten chickens are employed as a weight control and ten chickens as an infected control. The drug is given 48 hours in advance of the infection. One gm. of the test drug is mixed in a mechanical mixer with a sufficient amount of chicken feed to result in the desired dosage. The infection consists of approximately 200,000 oocysts given orally by pipette. The tests lasts for eleven days and the surviving birds are autopsied and examined for gross lesions in the ceca. The test birds are rated according to the number of survivors and the number of cecal lesions. The results are expressed as average degree of infection (A.D.I.). An average degree of infection of less than 2.5 is considered to be significant.

| Antibiotic | Conc. in Feed, PPM | Weight Gain % | Mort. % | Ave. Degree Infect. | | |
|---|---|---|---|---|---|---|
| Activity Against *E. Tennella* | | | | | | |
| Uninfected untreated control | 0 | 100 | 0 | 0.0 | | |
| Infected untreated control | 0 | 60 | 20 | 3.0 | | |
| Lasalocid | 75 | 98 | 0 | 0.0 | | |
| X-14934A | 100 | 21 | 0 | 0.0 | | |
|  | 25 | 25 | 0 | 0.0 | | |
|  | 10 | 101 | 0 | 0.6 | | |
| Activity Against Mixed Infection* | | | | | | |
|  |  |  |  | Upper | Mid | Ceca |
| Uninfected untreated control | 0 | 100 | 0 | 0.0 | 0.0 | 0.0 |
| Infected untreated control | 0 | 34 | 20 | 3.0 | 3.0 | 3.1 |
| X-14934A sodium salt | 5 | 44 | 40 | 3.1 | 3.1 | 3.2 |
|  | 10 | 65 | 20 | 2.7 | 2.4 | 2.7 |
|  | 15 | 62 | 0 | 2.0 | 2.0 | 2.0 |

*500,000 oocysts of mixed Eimeria species including a monensin-resistent *E. tennella* strain.

The coccidiostat compositions of this invention containing as the active ingredient, crystalline antibiotic X-14934A, or its pharmaceutically acceptable salts, or the dried unfiltered broth are prepared by mixing the active ingredient with an inert ingredient. The inert ingredient can comprise a feedstuff, extender materials and the like. By the term "inert ingredient" is meant a material which does not function as an antiparasitic agent, e.g., a coccidiostat, is inactive with respect to the active ingredient and which may be safely ingested by the animals to be treated, and thus, such inert material is one which is inactive for the purpose of the present invention.

The active ingredient when orally administered to coccidiosis susceptible domestic fowl, particularly turkeys and chickens, as a component of feed, effectively controls the disease by either preventing it or curing it after it occurs. Furthermore, the treated fowl either maintain their weight or actually gain weight when compared to controls. Thus, the compositions of this invention not only control coccidiosis, but also, aid in improving the efficiency of conversion of feed to weight gains.

The actual concentration of the active ingredient in animal feed can, of course, be adjusted to the individual needs and may vary over a wide range. The limiting criteria of the concentration are that the minimum concentration is such that a sufficient amount of active ingredient is provided to effect the desired control of coccidiosis and the maximum concentration is such that the amount of composition ingested does not result in any untoward or undesirable side effects.

Thus, for example, a feed premix or complete feed contains sufficient active ingredient to provide from about 1 ppm to about 20 ppm by weight of the daily feed consumption. Preferable, about 10 ppm to 15 ppm by weight is used. Generally, about 1 ppm to about 15 ppm of the active ingredient is sufficient for the purpose of controlling and combating coccidiosis. Amounts greater than 20 ppm, while being effective against coccidiosis, do not generally show improved results over the preferred ppm range and in some cases may adversely affect the growth, feed efficiency and mortality.

The optimum dose level will, of course, vary with the size of the animal. When using antibiotic X-14934A in accordance with the invention for treating or preventing coccidiosis, it can be first compounded or blended with a feed ingredient or carrier to become a feed additive premix, a feed concentrate, or a feed additive supplement. A feed additive, concentrate or premix is an article intended to be diluted to produce a complete feed, i.e., an article intended to be administered as a sole ration. A feed additive supplement is an article intended for consumption by an animal directly or which can be further diluted to produce a complete feed or can be ingested and used as a supplement to other rations. Feed additive supplements, concentrates and premixes contain a relatively large percentage of coccidiostats, i.e., the active ingredient, and are conveniently prepared by adding the active ingredient to a suitable carrier and mixing in a manner to give substantially uniform dispersion of the coccidiostat in the carrier. Suitable carriers are solids that are inert with respect to the active ingredient and which may safely be ingested by the animals to be treated. Typical of such carriers are commercial poultry feeds, ground cereal grains, grain by-products, plant protein concentrates, (soy, peanuts, etc.) fermentation by-products, salt, limestone, inorganic compounds, and the like or admixtures thereof. Liquid dispersions can be prepared by using water or vegetable oil preferably including a surface active agent, emulsifying agent, and the like in the liquid dispersion such as ethylene diamine tetraacetic acid, etc. and solubilizers. Any suitable carrier or extender material can function as the inert ingredient in the solid form of the antiparasitic agent provided that it is inert to the active material and is non-toxic insofar as the animal to which it is to be administered is concerned.

The active ingredient may be blended into a mash, pellet, or any desired configuration with the inert carrier or extender solid material by any convenient technique. For example, compositions can be formed by finely grinding or pulverizing the active ingredient and the inert ingredient using any commercially available grinder or pulverizer with or without the feed material being present. If the feed material is not present when the grinding or pulverizing is effected, the resultant material can be distributed, in accordance with the present invention, in any conveniently available feed material. Typical poultry feeds which can be medicated with active ingredient of this invention can contain several ingredients, for example, they can contain high energy grain products such as corn, wheat, wheat red dog flour, milo, oatmeal, or the like; medium and low energy grain products, such as oats, barley, wheat flour, middlings, standard middlings or the like; stabilized fats; vegetable protein such as soybean meal, corn gluten meal, peanut meal, or the like; animal protein such as fish meal, fish solubles, meat scraps or the like; UGF (unidentified growth factor) sources and other B-vitamin carriers such as dried milk products, dried brewers yeast, distillers dried solubles, fermentation solubles, or the like; dehydrated alfalfa meal; and various special additives such as additional riboflavin, vitamin $B_{12}$, calcium pantothenate, niacin, choline; vitamin K and vitamin E or the like, as well as stabilized vitamin A, vitamin $D_3$ (D-activated animal sterols); calcium and phosphorus supplements such as dicalcium phosphate, steamed bone meal, defluorinated phosphate, limestone, or the like; iodized salt, manganese sulfate, zinc carbonate, an antibiotic feed supplement; methionine or its hydroxy analog, and an antioxidant.

As is evident from the above, the coccidiostat compositions are intended for oral ingestion. They can be added to the normal feed supply of the treated animal or can be administered by other procedures, such as incorporating the same in a tablet, pill, or bolus and supplying it forcibly to the animal. The administration of the active ingredient must be considered in terms of the specific animal under the husbandry practices encountered.

A suitable medicated poultry feed intended as a starter feed for broilers is prepared by blending 10-15 ppm by weight of antibiotic X-14934A in a basic poultry ration consisting of:

| Ingredients: | | |
|---|---|---|
| Corn meal, No. 2, yellow, ground | pounds/ton | 1.123 |
| Stabilized grease or vegetable oil | " | 60 |
| Soybean oil meal (low fiber content 50% protein) | " | 480 |
| Corn gluten meal | " | 50 |
| Fish meal, antioxidant treated, 60% protein | " | 30 |
| Fish solubles, dried basis | " | 10 |
| Meat and bone scraps, 50% protein | " | 140 |
| Corn distillers dried solubles | " | 50 |
| Alfalfa meal, 17% protein 100,000 A/lb. | " | 30 |
| Salt iodized | " | 5 |
| Manganese sulfate, feed grade | " | 0.75 |
| Zinc carbonate or oxide | " | 0.25 |
| Riboflavin, | grams | 3 |
| Vitamin $B_{12}$ | mg. | 6 |
| Calcium pantothenate | gms. | 5 |
| Niacin | " | 30 |
| Stabilized vitamin A USPI units | | 6,000,000 |
| Vitamin $D_3$ I.C. | | 650,000 |
| Vitamin E acetate I.U. | | 5,000 |
| Vitamin E (menadione sodium bisulfite) | grams | 2 |
| DL-methionine or analog | pounds/ton | 1 |
| Antioxidant (ethoxyquin or butylated hydroxy toluene) | " | 0.25 |

Similar feeds can be prepared containing the antibiotic at other concentrations, set forth herein as well as in the form of the dried unfiltered broth in such amount as to give the same concentrations of active antibiotic.

Antibiotic X-14934A also exhibits activity as a feed efficiency enhancer in ruminants. The compound is active, i.e. shifts volatile fatty acid ratios to reflect increased propionate levels, at levels of about 50 ppm.

What is claimed:

1. A method of treating coccidiosis in susceptible domestic fowl which comprises treating said fowl with a coccidiostatic effective amount of a compound of the formula

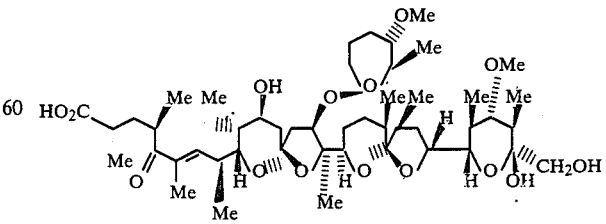

or a pharmaceutically acceptable salt thereof in a suitable carrier medium.

* * * * *